United States Patent
Leon et al.

(10) Patent No.: US 6,610,042 B2
(45) Date of Patent: Aug. 26, 2003

(54) DISPOSABLE UNIT-DOSE JET-INJECTION SYRINGE FOR PRE-FILLED AND/OR TRANSFILLED LIQUID INJECTABLE MEDICAL DRUG OR VACCINE PRODUCTS AND METHOD THEREOF

(75) Inventors: Nathaniel Leon, Overland Park, KS (US); Phillip L. Gerwig, Perrysville, OH (US)

(73) Assignee: Felton Medical, Inc., Lenexa, KS (US)

( * ) Notice: Subject to any disclaimer, the term of this patent is extended or adjusted under 35 U.S.C. 154(b) by 0 days.

(21) Appl. No.: 09/783,444

(22) Filed: Feb. 14, 2001

(65) Prior Publication Data

US 2002/0065483 A1 May 30, 2002

(Under 37 CFR 1.47)

Related U.S. Application Data (63) Continuation-in-part of application No. 09/205,621, filed on Dec. 4, 1998, now abandoned.
(60) Provisional application No. 60/067,803, filed on Dec. 5, 1997.

(51) Int. Cl.$^7$ .............................................. A61M 31/00
(52) U.S. Cl. ................... 604/500; 604/68; 604/232; 604/187; 604/183; 604/218; 222/326
(58) Field of Search ...................... 604/68–72, 232–235, 604/500, 124, 125, 131, 187, 134–136, 181, 183, 200, 218, 227, 236, 244, 403, 408, 231, 411–415; 222/631, 386, 324–327, 372

(56) References Cited

U.S. PATENT DOCUMENTS 3,462,867 A    8/1969  Zimmet et al.
3,540,444 A   11/1970  Moreland
3,946,732 A    3/1976  Hurscham
4,031,892 A    6/1977  Hurschman
4,124,024 A   11/1978  Schwebel et al.
4,165,739 A    8/1979  Doherty et al.
4,421,508 A   12/1983  Cohen (List continued on next page.)

FOREIGN PATENT DOCUMENTS

WO     0117592    3/2001

OTHER PUBLICATIONS

Genesis Medical Technologies Inc. website information on http://www.geocities.com/~genmedtech/information.htm#product.
Figge, et al., *Anatomic Evaluation of a Jet Injection Instrument Designed to Minimize Pain and Inconvenience of Parental Therapy*, The American Practitioner, vol. 3, No. 4, pp. 197–206 (Dec. 1948).

*Primary Examiner*—Brian L. Casler
*Assistant Examiner*—Cris L Rodriguez
(74) *Attorney, Agent, or Firm*—Mayer, Brown, Rowe & Maw; Joseph A. Mahoney; Christine M. Rebman (57) ABSTRACT

A disposable unit-dose jet injection syringe having a cylindrically shaped syringe body. The syringe body has a rear open end and a forward closed end. The rear open end has an enlarged diameter forming a flange that retains the syringe to the driving system during the injection cycle. The closed end has an small area coined by a stamping process. A jet orifice is punched through the small area of the closed end. A cavity formed in syringe body is configured to hold a unit dose of liquid, drug, or biological. A piston is slidably engaged within the body to inject the unit dose. A driving system activates the piston to inject the unit dose out of the jet orifice. A method of manufacturing a jet injection syringe is also provided. A method of injecting a medicine is also provided.

10 Claims, 4 Drawing Sheets

U.S. PATENT DOCUMENTS

| | | | |
|---|---|---|---|
| 4,507,113 A | | 3/1985 | Dunlap |
| 4,518,385 A | * | 5/1985 | Lindmayer et al. ............ 141/2 |
| 4,592,742 A | | 6/1986 | Landau |
| 4,596,556 A | | 6/1986 | Morrow et al. |
| 4,662,878 A | | 5/1987 | Lindmayer |
| 4,874,367 A | | 10/1989 | Edwards |
| 4,883,483 A | | 11/1989 | Lindmayer |
| 4,913,699 A | * | 4/1990 | Parsons ....................... 604/68 |
| 5,009,637 A | * | 4/1991 | Newman et al. ............ 604/143 |
| 5,024,656 A | * | 6/1991 | Gasaway et al. ........... 604/141 |
| 5,062,830 A | | 11/1991 | Dunlap |
| 5,181,909 A | * | 1/1993 | McFarlane ................. 604/191 |
| 5,279,608 A | | 1/1994 | Cheikh |
| 5,304,128 A | | 4/1994 | Haber et al. |
| 5,312,335 A | | 5/1994 | McKinnon et al. |
| 5,334,144 A | | 8/1994 | Alchas et al. |
| 5,354,286 A | | 10/1994 | Mesa et al. |
| 5,383,851 A | | 1/1995 | McKinnon et al. |
| 5,399,163 A | | 3/1995 | Peterson et al. |
| RE35,167 E | | 3/1996 | Mouchawar et al. |
| 5,501,666 A | | 3/1996 | Spielberg |
| 5,503,627 A | | 4/1996 | McKinnon et al. |
| 5,520,639 A | | 5/1996 | Peterson et al. |
| 5,536,249 A | | 7/1996 | Castellano et al. |
| 5,569,189 A | | 10/1996 | Parsons |
| 5,593,390 A | | 1/1997 | Castellano et al. |
| 5,599,302 A | | 2/1997 | Lilley et al. |
| 5,697,917 A | | 12/1997 | Sadowski et al. |
| 5,704,911 A | | 1/1998 | Parsons |
| 5,716,346 A | | 2/1998 | Farris |
| 5,722,953 A | | 3/1998 | Schiff et al. |
| 5,728,074 A | | 3/1998 | Castellano et al. |
| 5,746,714 A | * | 5/1998 | Salo et al. .................. 604/143 |
| 5,746,733 A | | 5/1998 | Capaccio et al. |
| 5,755,696 A | | 5/1998 | Caizza |
| 5,769,138 A | | 6/1998 | Sadowski et al. |
| 5,776,125 A | | 7/1998 | Dudar et al. |
| 5,782,802 A | | 7/1998 | Landau |
| 5,800,388 A | | 9/1998 | Schiff et al. |
| 5,832,971 A | | 11/1998 | Yale et al. |
| 5,833,213 A | | 11/1998 | Ryan |
| 5,836,923 A | | 11/1998 | Mayer |
| 5,839,715 A | | 11/1998 | Leinsing |
| 5,846,233 A | | 12/1998 | Lilley et al. |
| 5,851,198 A | | 12/1998 | Castellano et al. |
| 5,899,879 A | * | 5/1999 | Umbaugh ................... 604/68 |
| 5,899,880 A | | 5/1999 | Bellhouse et al. |
| 5,938,637 A | | 8/1999 | Austin et al. |
| 6,013,050 A | | 1/2000 | Bellhouse et al. |
| 6,083,197 A | | 7/2000 | Umbaugh |
| 6,096,002 A | | 8/2000 | Landau |
| 6,183,449 B1 | | 2/2001 | Sibbitt |
| 6,241,709 B1 | | 6/2001 | Bechtold et al. |
| 6,258,062 B1 | | 7/2001 | Thielen et al. |
| 6,364,865 B1 | | 4/2002 | Lavi et al. |

* cited by examiner

DISPOSABLE UNIT-DOSE JET-INJECTION SYRINGE FOR PRE-FILLED AND/OR TRANSFILLED LIQUID INJECTABLE MEDICAL DRUG OR VACCINE PRODUCTS AND METHOD THEREOF

RELATED APPLICATIONS

This application is a continuation-in-part of U.S. patent application Ser. No. 09/205,621, filed Dec. 4, 1998, now abandoned which is based on, and claims priority to, U.S. Patent Application Serial No. 60/067,803, filed Dec. 5, 1997, now abandoned the disclosures of which are hereby incorporated herein by reference to the extent permitted by law.

FIELD OF THE INVENTION

The present invention generally refers to jet-injection syringes and, more particularly, to disposable unit-dose jet injection syringes.

BACKGROUND OF THE INVENTION

Jet injection instruments were being developed as early as the 1940's. The developments included a hypospray injector, which regulates the dosage, with an attached body containing the drug. F. H. J. Figge & D. J. Barnett, *Anatomic Evaluation of a Jet Injection Instrument Designed to Minimize Pain and Inconvenience of Parental Therapy*, AMER. PRACTITIONER 197–206 (December 1948). Several jet-injection systems with reusable syringes are known. The reusable systems, however, have proven to offer little if any protection for cross contamination between subjects. In light of research that many diseases can be passed between subjects via jet injections, e.g. HIV, hepatitis, etc., these reusable systems become an unacceptable method for mass injection and/or vaccination.

There have been attempts to overcome the problem of cross contamination by offering jet-injection systems with disposable plastic jet-injection syringes. While these disposable plastic jet-injection syringes have somewhat overcome the potential for cross contamination, they introduce several other problems such as incompatibility with long term storage and increased manufacturing costs.

These plastic jet-injection syringes are made of a limited family of polymers, mostly polycarbonate, that can withstand high pressures associated with jet injection (in the range of 2000 to 10,000 psi). These polymers, however, have either a limited or no long-term shelf life because of the potential leaching of chemical extractables from the polymers into the liquid compound to be injected thereby causing contamination.

The plastic jet-injection syringes also require a relatively thick wall section to withstand the large pressure spike produced during jet injection. The microscopic orifice needed to obtain sufficient fluid velocity for skin penetration and subsequent deposition of the liquid requires that the liquid must travel a relatively long distance to pass through the thick wall. The ratio of orifice length to orifice diameter is typically over 10:1. This long distance in relationship creates a high manufacturing cost to form the orifice and creates several further technical difficulties. First, the high length-to-diameter ratio is difficult to produce with consistent orifice quality. Second, the high length-to-diameter ratio generates velocity loss, thereby requiring a greater initial force to achieve the required injection velocity which adds cost and greater bulk to the pressure generation system.

Injectable medications for human applications are traditionally supplied to the end user, not in the syringe that will be used to inject the medication into the patient, but in a secondary container, or multiple secondary containers for the case of lyophilized vaccines. Before the medication can be injected into the patient, it must be transferred into the syringe, which is filled to the appropriate level (trans-filled).

Another problem associated with existing systems is the lack of an efficient and safe method for transfilling an empty sterile unit dose syringe with liquid compound from a bulk source. There have been several attempts to address this problem with varying degrees of success. Most methods employ a needle or compound bottle puncturing spike temporarily attached to the jet injection syringe. Liquid is drawn from the bottle into the syringe through the needle or spike by a vacuum created when a piston is retracted in the syringe. There are a number of unit dose needle free injection or jet injection systems available on the market today (Bioject®, J-tip®, Injex®, etc.). For all these devices, the accepted method of filling the injector cartridge emulates the same procedure that is used for filling a standard needle injector. This is a slow, some times messy (because of the nature of the distal end of the jet injector syringe), and potentially hazardous operation (in reference to the use of a needle and potential needle stick injury) for transfilling appears to be at cross-purposes with the primary goal of eliminating sharps from the administration of medications.

Accordingly, there is a need in the art for an improved disposable jet-injection syringe and method of making the same which allows long term shelf life without leaking chemicals and can be produced at a relatively low cost. Further, there is a need in the art for an improved disposable jet-injection syringe with a metal thin wall which reduces the piston length, reduces manufacturing costs, reduces inconsistent orifice quality, and reduces piston force while withstanding piston pressure. Additionally, there is a need in the art for an improved device and method for transfilling an empty sterile unit dose syringe which is efficient and safe without the need of needles that would present sharps hazards to medical personnel. Additionally, there is a need in the art for an improved device which can be transfilled from a bulk source. Further, there is a need of transfilling from a bulk source which can be transfilled from an end located away from the injection area. Additionally, there is a need in the art for a method of manufacturing an improved disposable jet injection syringe. Accordingly, there is a need in the art for a method of injecting medication with an improved disposable jet injection syringe.

SUMMARY OF THE INVENTION

Disclosed is a disposable unit-dose jet injection syringe having a cylindrically shaped body. The body has a rear open end and a forward closed end with a cavity disposed therebetween. The rear open end has an enlarged diameter forming a flange that retains the syringe to a driving system during the injection cycle. The closed end has a small area coined by a stamping process. A jet orifice is punched through the small area of the closed end. The thickness of the coined area may be substantially equal to the diameter of the orifice. A piston is movably positioned within the syringe body to form a cavity for holding a unit dose of liquid, powder, drug, or biological.

The present invention further relates to a method of manufacturing a unit-dose jet injection syringe comprising stamping a body. Next, the method forms a forward closed end and a rear open end on the body. Then, a jet orifice is stamped through the forward closed end. The method then provides injection molding a piston from a polymer material and removably attaching the piston inside the metal body. The present invention further provides a method of injecting medicine comprising connecting a disposable syringe having a cavity to a driving system. A piston is then activated through the cavity. The method next provides injecting the unit dose by the piston through a jet orifice into a subject. After the unit dose has been injected, the disposable syringe is disconnected.

The present invention further relates to an apparatus and method for transfilling a disposable unit-dose jet injection syringe.

BRIEF DESCRIPTION OF THE DRAWINGS

These and further features of the present invention will be apparent with reference to the following description and drawings, wherein.

DETAILED DESCRIPTION OF PREFERRED EMBODIMENTS

Figures 1, 2:
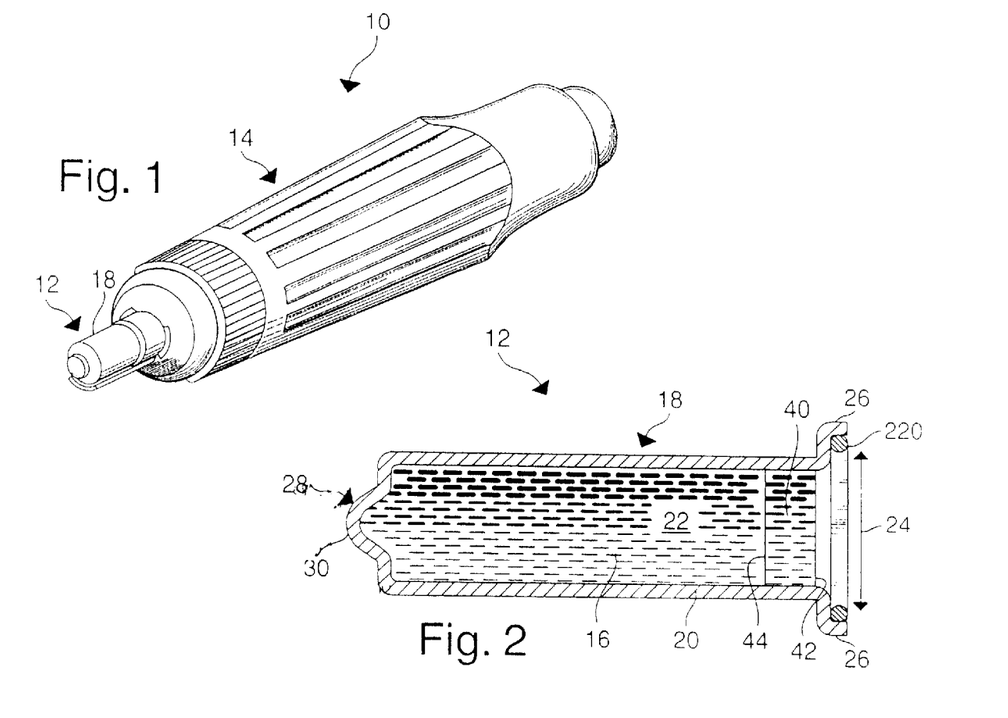
FIG. 1 is a top side view of a single-dose jet injection system including a disposable unit-dose jet injection syringe according to the present invention.
FIG. 2 is a cross-sectional view of a disposable unit-dose jet-injection syringe according to the present invention.

FIG. 1 illustrates a single-dose jet-injection system 10 that is designed to inject a single dose of medicine into a subject (not shown). System 10 includes a disposable syringe 12 for holding a unit dose 16 (FIG. 2) of medicine to be jet injected into a subject and a driving system 14 for injecting unit dose 16 from the disposable syringe 12 during an injection cycle as described in more detail hereinafter. The driving system 14 may be pneumatically operated by any power system as is generally known in the art, including but not limited to the Bio-Jet® or the spring powered Vita-Jet®. The unit dose 16 includes, but is not limited to, liquid compounds such as a liquid vaccine and powders such as lyophilized vaccines, including reconstituted lyophilized vaccines such as MMR trivalent vaccine, for example. The unit dose 16 may also include but is not limited to a biological compound and a drug compound.

As best shown in FIG. 2, the disposable syringe 12 includes a body 18 and a piston 40 located within body 18. Body 18 and piston 40 together form a cavity 22 for holding the unit dose 16 of medicine. Cavity 22 can be either prefilled or transfilled with unit dose 16 as discussed in more detail hereinafter.

Figure 3:
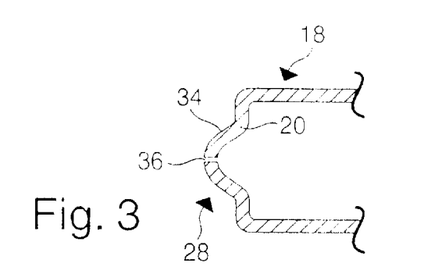
FIG. 3 is a side view of he closed end of the syringe body of FIG. 2 after coining to a reduced wall thickness and punching an orifice.

As best shown in FIGS. 2 and 3, the body 18 of the disposable syringe 12 is formed by a deep drawn, thin, wall, metal stamping. The use of a deep drawn metal stamping, which can be formed by either transfer press or progressive die method, generates a relatively low cost body 18 capable of withstanding high injection pressures associated with jet injection, while maintaining a relatively thin wall 20. The thin wall 20 preferably has a thickness in the range of about 0.018 inches to about 0.025 inches. Therefore, a burst factor of approximately 3:1 is obtained for typical jet injection pressures when the body 18 has an inner diameter of about 0.25 inches. The body 18 is preferably formed from metal or any material which is relatively inert, including but not limited to 316 stainless steel or medical grade steel, which have a high tensile strength in comparison to polymers typically used in disposable jet-injection syringes. Additionally, the body 18 may be made of any suitable material which will not react with the unit dose 16 resulting in a longer storage life of the system 10.

The body 18 is generally cylindrically-shaped with a rear open end 24 and a forward closed end 28 where the rear open end 24 has an enlarged diameter as shown in FIG. 2. The enlarged diameter forms a flange 26 that retains the disposable syringe 12 to the driving system 14 during the injection cycle. The forward closed end 28 is formed with a "skin stretching" shape that aids in reducing the liquid jet velocity necessary for skin penetration. The shape is generally a hemispherically shaped and outwardly extending protrusion. An exterior surface 30 of closed end 28 may have groves (not shown) formed therein. Wherein the grooves may be formed by the stamping process, which assists in avoiding slippage of contract with the closed end 28 on the skin of the subject. The thin metal wall 20 also quickly warms upon contact with the subject. Therefore. "cold shock" discomfort is minimal.

FIG. 3 depicts another embodiment of the present invention. Forward closed end 28 further includes a small area 34 (or alternatively areas), which is reduced to a smaller thickness. Small area 34 can be coined in the stamping process with a frusto-conical shaped punch for strength of the punch and to allow clearance for a subsequent orifice punch. The small area 34 has a relatively small diameter such as, for example, about 0.020 inches (but larger than the diameter of a jet orifice 36).

Figure 4:
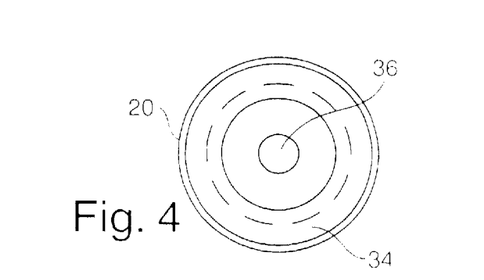
FIG. 4 is an end view of the syringe of FIG. 2.

The jet orifice 36 is punched through the small area 34 according to standard stamping hole diameter-to-thickness ratios, as depicted in FIG. 4. Note that with smaller diameter jet orifices 36 it may be necessary to have multiple jet orifices 36. In one embodiment, the diameter of the jet orifice (or orifices) 36 is preferably in the range of about 0.002 inches to about 0.015 inches. The orifice length-to-diameter ratio can be approximately 3:1 to obtain a quality jet orifice 36 and long punch tool life. For the jet orifice 36 to have diameter of about 0.0006 inches, the small area 34 would need a coined wall thickness of about 0.018 inches to obtain the 3:1 ratio. Excellent results are also obtained with varied diameters of the jet orifice 36 with respect to the wall thickness 20 of the small area 34.

The relatively short distance the unit dose 16 travels in relationship to the diameter of the jet orifice 36 is sufficient to focus a stream, out of the jet orifice 36 to contact the skin of the subject. Unit dose 16 acts as a solid projectile coming from a gun barrel, due to its high velocity, and not like a typical nozzle which creates a coherent stream in open atmosphere. A jet injection stream of the unit dose 16 fired into ballistic gelatin generates a pattern similar to a firearm bullet, except on a smaller, more controlled scale.

The material around the jet orifice 36 may withstand injection pressures based on the small area 34 that is thinned for orifice punching. For example, the small area 34 with an about 0.020 inch diameter and coined to about 0.006 inch thickness could theoretically withstand approximately 22,036 psi liquid pressure where the material is 316 stainless steel having a tensile strength of about 75,000 psi. This would provide a safety factor of more than 3:1 at typical injection pressures.

The inclusion of the step of orifice punching in the stamping process allows for a low cost method of producing a quality, precision jet orifice 36 with a low length-to-diameter ratio. This reduces velocity losses in the jet orifice 36 and lessens power demands, since it is not necessary to overcome higher orifice velocity losses due to higher length-to-diameter ratios. Another benefit of the orifice stamping process is that the process generates only a small slug for removal and cleaning whereas a typical drilling process creates a multitude of chips for removal and cleaning.

The body 18 can be coated on all surfaces with an ultrathin coating of an inert material. A suitable material includes, but is not limited to, poly-para-xylenes, commercially known as PARYLENE®, available from Specialty Coating Systems, Indianapolis, Ind. This coating is bonded to the metal surface and provides several benefits. The coating has a low coefficient of friction and reduces friction between the inside diameter of the body 18 and the outside diameter of the piston 40, thereby reducing the force needed to drive the piston 40 during the injection cycle and renders the benefits described hereinabove with regard to injection force reduction. The coating also eliminates any reactive tendencies between the unit dose 16 and the base material of the body 18 since it creates an inert barrier between the material and unit dose 16. Therefore, long term storage of the disposable syringe 12 can be enhanced. The coating also provides some thermal barrier properties to the skin contact section of the disposable syringe 12 to lessen subject discomfort from direct metal contact. Further, as to the metal embodiment of the body 18, the body 18 will not chemically break down, thereby preventing any leakage into the medicine and leading to a longer storage life.

Figure 6:
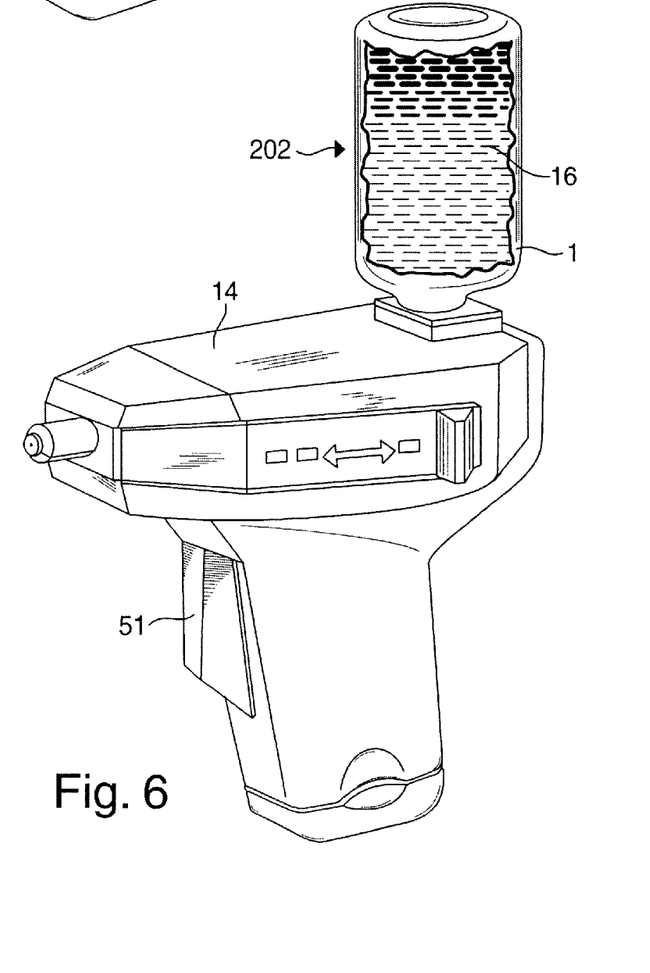
FIGS. 6 to 7 are views showing a multi-shot single-dose jet injection system including a disposable unit-dose jet-injection syringe according to the present invention.

The design of the piston 40 dictates the ultimate usage of the disposable syringe 12, that is, whether it is prefilled or transfilled with unit dose 16. The body 18 is preferably the same in either application. The prefilled application indicates that the cavity 22 of the disposable syringe 12 is prefilled with the unit dose 16 to present a certain medicine with a determined amount ready to be injected. The transfilled application indicates that the disposable syringe 12 is empty thereby requiring filling of the unit dose 16 from a bulk container 202 (FIG. 6). The piston 40 has common features, however, even though different versions are used for the different applications.

Figure 5:
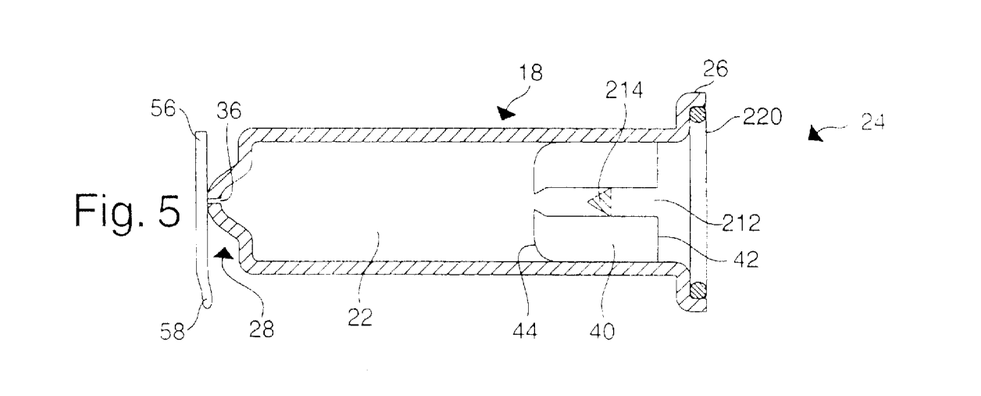
FIG. 5 is a cross-sectional view of a syringe for Tran filling according to the present invention.

Referring to FIGS. 2 and 5, the piston 40 is generally cylindrically shaped to closely fit within the body 18 to form the cavity 22 between the jet orifice 36 and the piston 40 such that when a force is applied to a rear end 42 of the piston 40, the piston 40 moves toward the jet orifice 36 and forces the unit dose 16 out through the jet orifice 36 and into the subject. Piston 40 is preferably injection molded from a relatively inert polymer, such as but not limited to, high density polyethylene (HDPE) or a medical grade rubber. HDPE has a relatively low coefficient of friction, thus reducing power requirements as discussed hereinabove. HDPE is also relatively inexpensive and allows rapid injection molding rates. Since HDPE is an excellent self-lubricated material for the manufacture of seals, an integral molded cup seal (not shown) can be on a leading edge 44 of the piston 40 that is self energized when a driving piston applies the necessary force to dispense the unit dose 16 in cavity 22 during the injection cycle. This eliminates the need for an elastomeric seal with a back-up TEFLON® pressure washer as used in existing disposable jet injection syringes reducing the associated assembly costs of these components. If necessary, piston 40 can be coated with the coating as previously described for chemical resistance and/or reduced friction.

The piston 40 depicted in FIG. 2 may be utilized with the disposable syringe 12 when it is prefilled. FIG. 5 depicts a piston 40 that may be utilized with disposable syringes 12 that may be transfilled. The piston 40 depicted in FIG. 5 includes an axial channel 212 communicating with the cavity 22 and the rear end 42 of the piston 40. Located in the channel 212 is a check valve 214 that allows flow into the cavity 22 and prevents flow out of the cavity 22. The check valve 214 is positive acting and the leak proof. The axial channel 212 provides a one-way pathway for the unit dose 16 from a bulk container 202 (FIG. 6) to the cavity 22 for loading the disposable syringe 12 to be transfilled. The syringe 12 may also include a frangible retaining ring 220 molding on the rear open end 24 of the body 18. Retaining ring 220 has a diameter larger than the bore of cavity 22 and is seated in the enlarged diameter at the rear open end 24 of the body 18. The enlarged diameter of the body 18 doubles into the flange 26 to retain the disposable syringe 12 in the driving system 14 and to seat the retaining ring 220.

Figure 7:
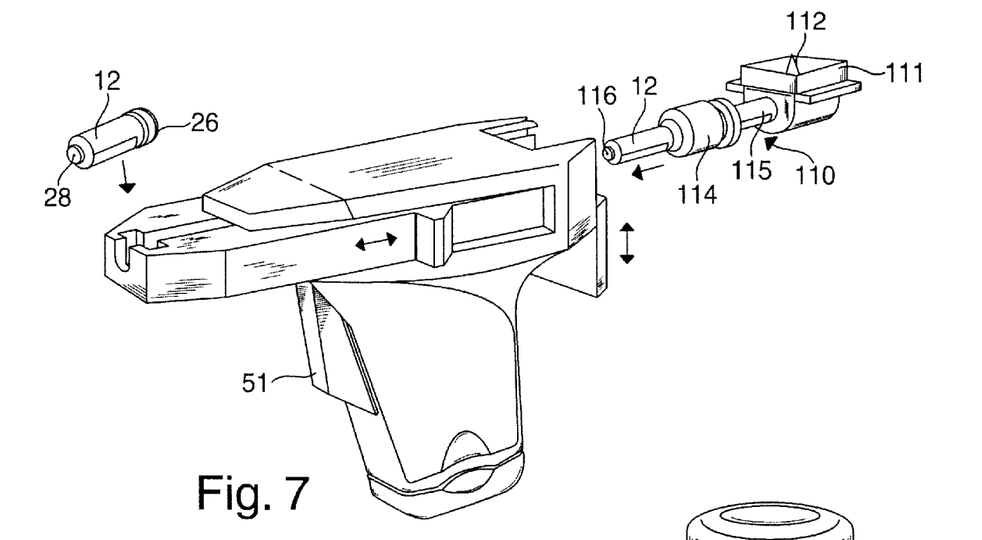

FIGS. 6–7 illustrate that the disposable syringes 12 of FIGS. 5, 8A–D and 9 may be transfilled from the bulk container 202 immediately before the injection. The bulk container 202 is detachably attached to the driving system 14 via a filler adapter 110. The filler adapter 110 includes a connector 111, a vent spike 112, a driving piston 114, a tube 115, and a dry break coupling 116. The connector 111 detachably attaches the bulk container 202 to the filler adapter 110. The vent spike 112, or other bottle septum interfaces as are generally known in the art, may be utilized to provide fluid communication between the bulk container 202 and the tub 115 of the filler adapter 110 and to control the release of the medicine from the bulk container 202. The driving piston 114 interfaces with the driving system 14 which produces the energy required to fill the syringe 12 and to dispense the unit dose 16. The dry break coupling 116 is located on the distal end 118 of the driving piston 114 of the filler adapter 110.

The retaining ring 220 (FIG. 5) allows the piston 40 to be forced onto the dry break coupling 116 of the driving piston 114 of the filler adapter 110. the dry break coupling 116 withdraws the piston 40 from the forward closed end 28 to the rear open end 24 during the transfilling process depicted in FIGS. 8A–D and 9. The unit dose 16 is transfilled from the bulk container 202 through the injection piston 40 through the control of the check valve 214. The unit dose 16 is then transfilled into the disposable syringe 12 via the channel 212. The filler adapter 110 may also be used to introduce reconstituting fluid into the cavity 22, such as would be the case if a lyophilized (freeze dried) vaccine product was pre-inserted in the cavity 22 as a per-loaded syringe.

Figure 8A:
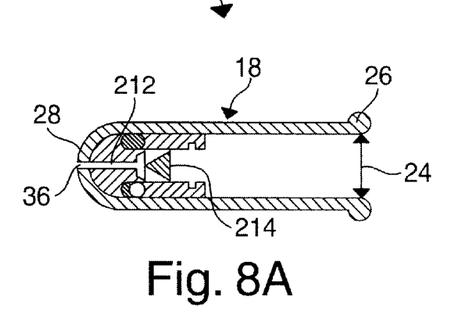
FIGS. 8A–D depict the operational sequence of the transfilling and injection of a liquid medicine according to the present invention.
Figure 8B:
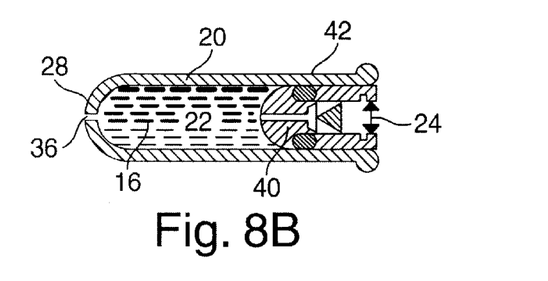
Figure 8C:
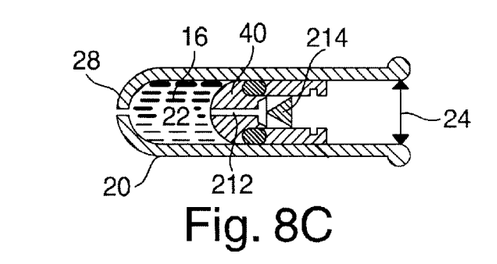
Figure 8D:
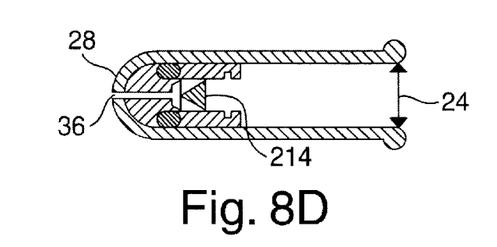
Figure 9:
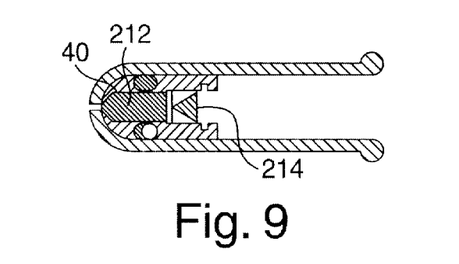
FIG. 9 is a cross sectional view of a transfilling syringe for a lyophilized medicine according to the present invention.

FIGS. 8A–D depict a transfilled syringe 12 utilized in injection a liquid medicine FIG. 9 depict a transfilled syringe 12 utilized in injection a lyophilized medicine. The piston 40 forms the cavity 22 between the jet orifice 36 and the piston 40 such that when a force is applied to a rear end 42 of the piston 40, the piston 40 moves toward the jet orifice 36 and forces the unit dose 16 out through the jet orifice 36 and into the subject. as depicted in FIGS. 8B–D. The piston 40 includes the axial channel 212. Located in the channel 212 is the check valve 214. The width of the axial channel 212 may vary depending on the nature of the medicine to be transfilled. For example, FIGS. 8A–D depict a relatively narrow axial channel 212 used in transfilling liquid medicines and FIG. 9 depict a wider axial channel 212 used in transfilling lyophilized medicines.

Figure 10:
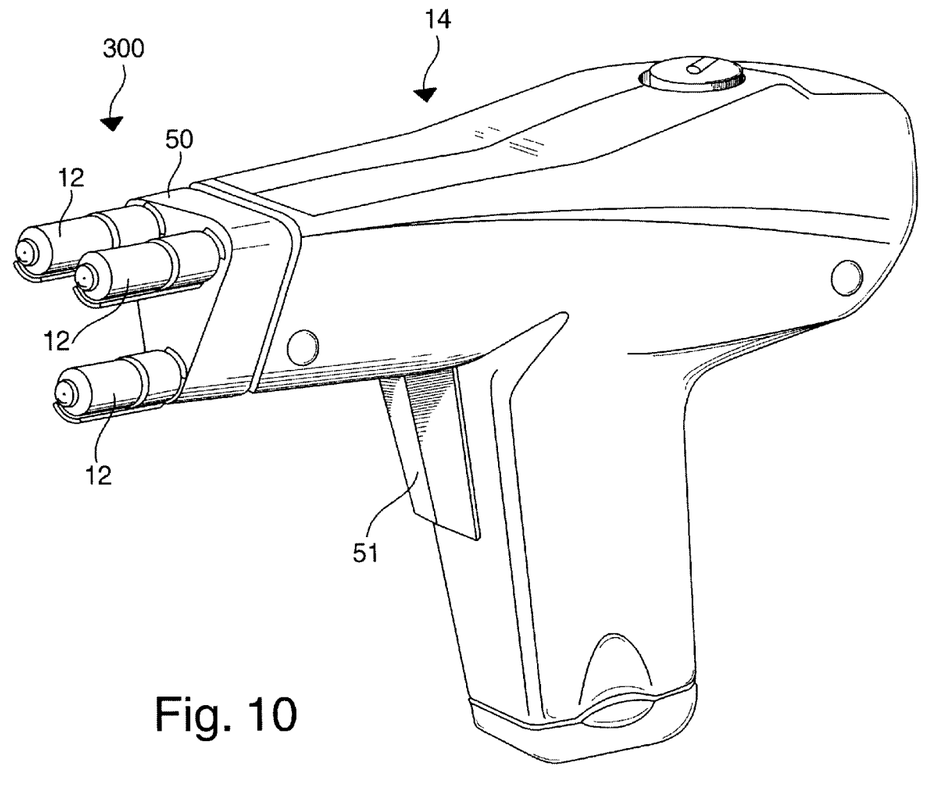
FIG. 10 depicts a multiple-dose jet injection system including several disposable unit-dose jet-injection syringes according to the present invention.

FIG. 10 illustrates a multiple-dose jet injection system 300 according to the present invention. System 300 illustrates that more than on disposable syringe 12 may be utilized to administer a variety of unit does 16 simultaneously. In one embodiment, system 300 includes three disposable syringes 12. The disposable syringes 12 may be prefilled or transfilled, as described above. In this embodiment, a plurality of disposable syringes 12 are removably attached to a mount 50. In this embodiment, each disposable syringe 12 is capable of holding the unit dose 16. The mount 50 is removably locked to the driving system 14 where an actuator 51 activates the driving system 14 to simultaneously inject the plurality of unit doses 16 with the subject. In another embodiment, the mount 50 may be rotated to individually inject each disposable syringe 12 into the subject. In another embodiment depicted in FIG. 7, the bulk container 202 may be removably attached to the driving system 14 via the connector 111 located opposite the forward closed end 28. Thus, the plurality of disposable syringes 12 which were loaded void of any unit dose 16 may be transfilled via the bulk container 202, in the manner described above.

For safety and sanitary conditions, the jet orifice 36 of the syringe 12 may be sealed after factor bulk unit dose filling, lyophilization, or on empty, sterile versions for transfilling. A form of medical grade shrink film 56 may be applied over closed end 28 of the disposable syringe 12 to keep contamination out and the liquid in, as depicted in FIG. 5. Film 56 may have tear-away tab 58 for removal prior to use or could be left on, in the case of the disposable syringe 12 which is prefilled, so that it is pierced by the jet liquid stream on injection.

The present invention also relates to a method of manufacturing the jet injection syringe. The method comprises stamping the body 18 from metal by a deep drawn progressive die. Next, the method provides forming the forward closed end 28 and the rear open end 24 on the body 18 with the cavity 22 in-between. The body 18 may also be flanged on the rear open end 24. The method then relates to punching the jet orifice 36 in the forward closed end 28.

Additionally, a piston 40 is manufactured by molding the piston 40 from a polymer material injection mold. The method then comprises installing the piston 40 to slidably engage inside the body 18. Further, in the manufacturing method, the body 18 and piston 40 are coated with an inert material and the molded cup seal (not shown) may be formed on the piston 40. In an another embodiment, an axial channel 212 may be formed within the piston 40 and a check valve 214 may be positioned within the piston 40.

In an alternate method, the body 18 may be stamped by a transfer press. Further, in an alternate embodiment, a protrusion may be extended on the forward closed end 28. The protrusion may be coined to a reduced wall thickness 20 to increase the tensile strength around the jet orifice 36.

The present invention also relates to a method of injecting medicine. The method comprises connecting the disposable syringe 12 pre-filled with the unit dose 16 to the driving system 14. The unit dose 16 may be a liquid medicine or a lyophilized medicine. The driving system 14 is fired once the prefilled disposable syringe 12 is locked onto the driving system 14 and is positioned on the subject. The driving system 14 drives the piston 40 forward into the body 18 and drives the unit dose 16 in the cavity 22 out of the syringe 12 through the jet orifice 36 and into the subject. After injection, the disposable syringe 12 is disconnected. In one embodiment, the film 56 is placed on the forward closed end 28 to keep contaminants out and the unit dose 16 in. In another embodiment, the tear away tab 58 of the film 56 is removed before the driving system is activated. The likelihood of accidental re-use of the disposable syringe 12 is decreased because the piston 40 is forced into closed end 28 of the body 18 upon injection.

In another embodiment, the disposable syringe 12 is note pre-filled; therefore, the method provides transfilling a unit dose 16 of medicine into the cavity 22 as depicted in FIGS. 7 and 8A–D. The bulk container 202 is detachably attached to the driving system 14 via the connector 111 of the filler adapter 110. The empty syringe 12 is connected to the driving system 14. The unit dose 16 is then drawn from the bulk container 202 by activating the driving system 14. The unit dose 16 travels through the vent spike 112 to the tube 115 of the filter adapter 110. The driving piston 114 interfaces with the driving system 14 which produces the energy required to fill the syringe 12. The medical grade shrink film (not shown), or other safety seal, may cover the forward closed end 28 of the empty syringe 12 to seal the jet orifice 36 so that a vacuum may be created when the driving system 14 is activated. The dry break coupling 116 withdraws the piston 40 from the forward closed end 28 to the rear open end 24 causing the unit dose 16 to travel to the cavity 22 through the channel 218 and check valve 214 positioned with the piston 40, as depicted in FIGS. 8B–8C.

Driving system 14 is also operated to inject the unit dose 16 once the disposable syringe 12 is filled with the unit dose 16. Driving piston 114 drives the piston 40 forward into the body 18 as the force generated by the driving piston 114 breaks off a retaining ring 220. The forward moving injection piston 40 drives unit dose 16 in cavity 22 out of the disposable syringe 12 through the jet orifice 36 and into the subject as depicted in FIGS. 8C–D. The likelihood of accidental re-use of the disposable syringe 12 is decreased because the disposable syringe 12 includes the one-use frangible retaining ring 220 and the piston 40 is forced into closed end 28 of the body 18 upon injection as depicted in FIG. 8A.

In an another embodiment depicted in FIG. 10, a plurality of disposable syringes 12 are connected to a mount 50 which is then attached to the driving system 14. The actuator 51 then activates the driving system 14 to either simultaneously or individually inject multiple unit doses 16 into the subject.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

What is claimed is:

1. A method of injecting a unit dose of medicine, comprising:
 a. connecting a bulk container of the unit dose to a driving system;
 b. connecting a syringe to the driving system, the syringe having a rear open end, a forward closed end and a cavity positioned in between;

c. drawing the unit dose from the bulk container through a channel in a piston in the cavity;

d. activating the piston through the cavity toward the forward closed end of the syringe; and e. injecting the unit dose by the piston through a jet orifice positioned on the forward closed end.

2. The method according to claim 1, wherein the unit dose comprises a liquid medicine.

3. The method according to claim 1, wherein the unit dose comprises a lyophilized medicine.

4. The method of claim 1, wherein drawing the unit dose from the bulk container through the channel in the piston in the cavity comprises drawing the unit dose through a check valve in the channel in the piston.

5. The method of claim 1, wherein connecting the bulk container of the unit dose to the driving system comprises:

(i) connecting the bulk container of the unit dose to a filler adapter; and (ii) connecting the filler adapter to the driving system.

6. The method of claim 5, wherein drawing the unit dose from the bulk container through the channel in the piston comprises a dry break coupling of the filler adapter withdrawing the piston from the forward closed end to the rear open end of the syringe.

7. A method for transfilling at least one syringe having a rear open end, a forward closed end and a cavity positioned in between with a unit dose of medicine comprising:

(a) connecting a bulk container of the unit dose to a filler adapter;

(b) connecting the filler adapter to a driving system;

(c) attaching the rear open end of the at least one syringe to the driving system;

(d) activating the driving system; and (e) drawing the unit dose from the bulk container through a channel in a piston in a cavity of the at least one syringe.

8. The method of claim 7, wherein drawing the unit dose from the bulk container through the channel in the piston comprises drawing the unit dose from the bulk container through the filler adapter to the channel in the piston.

9. The method of claim 7, wherein drawing the unit dose from the bulk container through the channel in the piston comprises drawing the unit dose from the bulk container through a check valve in the channel of the piston.

10. The method of claim 7, wherein drawing the unit dose from the bulk container through the channel in the piston comprises a dry break coupling of the filler adapter withdrawing the piston from the forward closed end to the rear open end of the at least one syringe.

* * * * *